(12) United States Patent
Oost et al.

(10) Patent No.: US 6,300,524 B1
(45) Date of Patent: Oct. 9, 2001

(54) PROCESS FOR PREPARING HIGHER UNSATURATED KETONES

(75) Inventors: Carsten Oost, Bad Dürkheim; Manfred Stroezel, Ilvesheim; Heinz Etzrodt, Neustadt; Dietmar Weller, Ludwigshafen; Udo Rheude, Otterstadt; Gerd Kaibel, Lampertheim; Thomas Krug, Worms; Luise Spiske, Seeheim-Jugenheim; Hagen Jaedicke, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/440,281

(22) Filed: Nov. 15, 1999

(30) Foreign Application Priority Data

Nov. 16, 1998 (DE) .............................. 198 52 691

(51) Int. Cl.$^7$ .................................. C07C 45/00
(52) U.S. Cl. ........................ 568/406; 568/383; 568/388; 568/391
(58) Field of Search ..................... 568/391, 346, 568/398, 356, 383, 388, 406

(56) References Cited

U.S. PATENT DOCUMENTS

| | | | |
|---|---|---|---|
| 4,173,588 | 11/1979 | Pasedach et al. | 260/595 |
| 4,310,705 | 1/1982 | Nissen et al. | 568/391 |
| 6,051,741 | * 4/2000 | Etzrodt et al. | 568/406 |

FOREIGN PATENT DOCUMENTS

| | | |
|---|---|---|
| 10 73 476 | 7/1960 | (DE) . |
| 0 022 955 | 1/1981 | (EP) . |
| 2 371 411 | 6/1978 | (FR) . |

OTHER PUBLICATIONS

Chemical Abstracts, vol. 102, No. 25, p. 553, Jun. 24, 1985, Jozef Gese, et al., "Unsaturated Ketones", Jul. 1, 1984.

* cited by examiner

*Primary Examiner*—Sreeni Padmanabhan
(74) *Attorney, Agent, or Firm*—Oblon, Spivak, McClelland, Maier & Neustadt, P.C.

(57) ABSTRACT

The present invention relates to an improved process for preparing higher unsaturated ketones by reacting the corresponding α,β-unsaturated alcohols with alkyl acetoacetates in a Carroll reaction , in a reactor system with fitted fractionation column, wherein A the α,β-unsaturated alcohol is introduced into the reaction vessel together with the organic aluminum compound in the absence of effective amounts of a solvent, and the alkyl acetoacetate is metered into this mixture, B a reaction temperature which is as constant as possible at between 175° C. and 220° C., preferably between 180° C. and 200° C., is adjusted and C during the reaction the content of alkyl acetoacetate in the reaction mixture is adjusted to a value which is as constant as possible at between 1 and 3% by weight.

It is advantageous in this process for the reaction temperature defined under B to be controlled by suitable variation of the heat input and/or by variation of the rate of addition of the alkyl acetoacetate, and for adequate mixing of the reaction mixture in the reaction vessel to be ensured This can be achieved with the aid of a stirrer, by pumping the reaction mixture through an external liquid circulation, by introducing the alkyl acetoacetate by means of a mixing nozzle or else by passing in a stream of inert gas.

The process according to the invention is particularly suitable for the Carroll reaction of higher alcohols such as 3,7-dimethyl-1,6-octadien-3-ol (linalool), 3,7-dimethyl-1-octen-3-ol, 3,7,11-trimethyl-1,6,10-dodecatrien-3-ol (nerolidol), 3,7,11-trimethyl-1-dodecen-3-ol or 3,7,11-trimethyl-1,6-dodecadien-3-ol (dihydronerolidol).

10 Claims, 2 Drawing Sheets

PROCESS FOR PREPARING HIGHER UNSATURATED KETONES

The present invention relates to an improved process for preparing higher unsaturated ketones by reacting the corresponding α,β-unsaturated alcohols with alkyl acetoacetates in a Carroll reaction.

Apart from the improvements according to the invention, this reaction is already known in its essential features. A reaction of this type between an unsaturated alcohol and an alkyl acetoacetate was described for the first time by Carroll in *J. Chem. Soc.* (London), 1940, pages 704 to 706. The range of application and the mechanism of this reaction were reported one year later by the same author in J. Chem. Soc. (London), 1941, pages 507 to 511.

One procedure for preparing 6,10,14-trimethyl-5-pentadecen-2-one by transesterification of ethyl acetoacetate with 3,7,11-tri-methyl-1-dodecen-3-ol in the presence of aluminum trialcoholates is to be found in French Patent 1 219 166 (of 1959). In this process, the reactants and the catalyst are introduced together into the reaction vessel and the reaction is carried out batchwise with removal of the alcohol liberated from the ethyl acetoacetate by distillation. In this case, the required ketone is obtained in 77% yield in a reaction time of about 10 hours.

This process is unsatisfactory for an industrial synthesis both because of the relatively long reaction times and because of the inadequate yields. The inadequate yields are particularly serious in the preparation of higher ketones, i.e. on use of higher alcohols of the formula II because the preparation thereof increases in cost as the chain length grows. Attempting to improve the yields by using the less costly component, in this case the alkyl acetoacetate, in excess easily leads to the formation of dehydroacetic acid as by-product which, on the one hand, deactivates the catalyst and, on the other hand, can be removed from the desired product only with difficulty. In addition, the dehydroacetic acid may crystallize out and thus block the outflow lines of the columns used.

A number of other patents describing some variants of the Carroll reaction are known. Thus, U.S. Pat. No. 2,795, 617 (of 1957) and DE AS 1 053 498 (of 1959) and CH 342 947 (of 1959), state that "although it is as a rule neither necessary nor desirable, it is possible to use a solvent in order to moderate the exothermic progress of the reaction". In the processes in these patents, the aluminum trialcoholate was added to the acetoacetate of the α,β-unsaturated alcohol, and the mixture was heated to reflux with vigorous stirring. Yields of up to 80% of theory were achieved thereby. The disadvantage of this process is that the preparation of the acetoacetate used as starting compound must take place in a preceding stage.

U.S. Pat. No. 2,839,579 (of 1958) and DE 1 078 112 (of 1960) report that the reaction can be carried out in a solvent. The appropriate acetoacetate is prepared by condensing the appropriate unsaturated alcohol with diketene in a separate stage.

DE 1 068 696 also states that the presence of a solvent might be advantageous. High-boiling solvents with boiling points far above the reaction temperature are mentioned in all cases.

Disadvantages of this process are that the yields stated in these patents are unsatisfactory for industrial use and, in particular, that an additional process stage is necessary to prepare the acetoacetate of the α,β-unsaturated alcohol, which leads to additional costs. The proposed presence of a high-boiling solvent moreover generally results in negligible increases in the yield and therefore leads only to a reduction in the space-time yield.

The Czech Patent 216 360 (of 1979) recommends carrying out Carroll reactions in a mixture of the unsaturated ketone to be expected as product of the reaction, and of methyl or ethyl acetoacetate, with the addition of an amount of the unsaturated alcohol which is just necessary to maintain the reaction. In this case, the reaction mixture is distilled to remove the carbon dioxide and a mixture of the unreacted unsaturated alcohol and methanol or ethanol, and the mixture is fractionated continuously in a connected distillation column. The α,β-unsaturated alcohol, which must have a boiling point below 180° C., is subsequently returned to the reaction. The yields achieved in this process with reaction times of 8 hours were about 80% of theory. This process has the disadvantage that the additional distillation column gives rise to additional capital and energy costs. In addition, the yields and reaction times in this process are unsatisfactory for a modern industrial process.

DE 2 928 944 (of 1979) further describes the preparation of α,β-unsaturated ketones by a Carroll reaction in the presence of small amounts of a solvent whose boiling point is between that of the alkyl acetoacetate employed and that of the alcohol to be eliminated therefrom. This solvent is referred to therein as "intermediate boiler". Possible inert intermediate boilers mentioned are appropriately boiling alcohols, esters, ethers, halogenated hydrocarbons and aromatic hydrocarbons, preferably aliphatic ketones having 4 to 7 C atoms. A particularly advantageous embodiment mentioned is the use of 2-methyl-3-buten-2-ol as reactive intermediate boiler, in which case an additional desired side reaction takes place by reaction thereof with the alkyl acetoacetate to give 2-methyl-2-hepten-6-one as another required product. The advantages mentioned on use of such an intermediate boiler are increased yields of product (about 95% of theory based on the alcohol, and about 85% of theory based on the acetoactate) and shorter reaction times (about 4–5 h) and thus high space-time yields. The reaction temperatures used in all the examples do not exceed 165° C.

However, the use of an intermediate boiler has not only advantages but also the following disadvantages. Thus, for example, on use of an inert intermediate boiler the reactor volume available for the precursors is reduced, i.e. the space-time yields which can be achieved are inevitably lower. In addition, for example, the presence of a reactive intermediate boiler such as 2-methyl-3-buten-2-ol, results in obligatory coupling of the production of different unsaturated ketones, which may be undesired.

It is an object of the present invention to improve the reaction of high-boiling α,β-unsaturated alcohols with alkyl acetoacetates in a Carroll reaction to give unsaturated ketones in such a way that it can also be carried out in the absence of a solvent or the absence of a so-called intermediate boiler, and thus without coupling with the preparation of other unsaturated ketones. It was moreover intended to achieve a higher yield of product, based on the unsaturated alcohol and based on the alkyl acetoacetate, with shorter reaction times, than in the syntheses described in the literature for the separate preparation of the unsaturated ketones. It was particularly intended to be able to prepare the ketones which are in demand as intermediates for preparing the essential vitamin E precursor isophytol, such as 6,10-dimethyl-5,9-undecadien-2-one (geranylacetone), 6,10,14-trimethyl-5,9,13-pentadecatrien-2-one (farnesylacetone), 6,10-dimethyl-5-undecen-2-one (dihydrogeranylacetone) and 6,10,14-trimethyl-5,9-pentadecadien-2-one (dihydrofarnesylacetone) with higher selectivity and higher space-time yield.

We have found that this object is achieved by a process for preparing unsaturated ketones of the general formula I

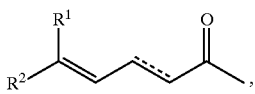
(I)

in which the dotted line may mean an additional C—C bond, $R^1$ is an alkyl group having 1 to 4 C atoms, and $R^2$ is a saturated or unsaturated aliphatic, cycloaliphatic or cycloaliphatic-aliphatic radical having 4 to 30 C atoms, by reacting the corresponding α,β-unsaturated alcohols of the general formula II

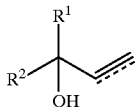
(II)

with alkyl acetoacetates of the general formula III

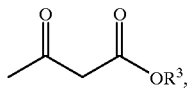
(III)

in which $R^3$ is alkyl having 1 to 4 carbon atoms, in the presence of from 0.1 to 5 mol %, based on the alkyl acetoacetate to be reacted, of an organic aluminum compound as catalyst with elimination and continuous removal by distillation of the carbon dioxide which forms during the reaction and of the alcohol of the general formula IV $$R^3—OH \quad (IV)$$

which is eliminated from the acetoacetate in a reactor system with fitted fractionating column, wherein A the α,β-unsaturated alcohol is introduced into the reaction vessel together with the organic aluminum compound in the absence of effective amounts of a solvent or of an intermediate boiler, and the alkyl acetoacetate is metered into this mixture, B a reaction temperature which is as constant as possible at between 175° C. and 220° C., preferably between 180° C. and 200° C., is adjusted and C during the reaction the content of alkyl acetoacetate in the reaction mixture is adjusted to a value which is as constant as possible at between 0.1 and 10% by weight, preferably between 1 and 3% by weight.

The process is particularly advantageous when the amounts of the reactants employed is chosen to result in a molar ratio of alcohol to alkyl acetoacetate of between 0.8 and 1.2, preferably between 0.95 and 1.05.

The yields of product in the described process are about 95% of theory based on the alcohol. The selectivity of the reaction, i.e. the yield based on the reacted alcohol, is in fact more than 97% of theory, so that overall yields of almost 100% can be achieved with the option of returning the unreacted alcohol. The yields of product based on alkyl acetoacetate are between 90% and 95% when this reactant is completely broken down. If complete breakdown of the alkyl acetoacetate is unnecessary, the selectivity based on the alcohol can be increased by up to 2% on use of the acetoacetate in excess (molar ratio of alcohol to acetoacetate between 0.7 and 0.9). However, in this case losses of selectivity based on acetoacetate must be expected, so that this procedure is worthwhile only for high-cost alcohols. Returning unreacted reactants is worthwhile in every case.

It was very surprising that on use of the conditions according to the invention, i.e. in particular despite the absence of a solvent or of an intermediate boiler and use of reaction temperatures of 175 to 220, preferably 180 to 200° C., scarcely any side reactions occur and it was thus possible to achieve excellent selectivities and moreover high space-time yields of the unsaturated ketones. This is t rue in particular because it was shown in the description of DE A 29 28 944 on the basis of comparative tests that considerably poorer selectivities were achieved under the reaction conditions usual therein but without addition of intermediate boilers.

The process according to the invention can in principle be applied to all known variants of the Carroll reaction in which the unsaturated alcohol has a higher boiling point than the alkyl acetoacetate. However, the process has particular importance for preparing unsaturated ketones required for preparing isophytol, an essential precursor of vitamin E, i.e. essentially α,β-unsaturated ketones which are formed when an alcohol of the general formula II in which $R^1$ is an alkyl group having 1 to 4 C atoms and $R^2$ is a group of the general formula VI

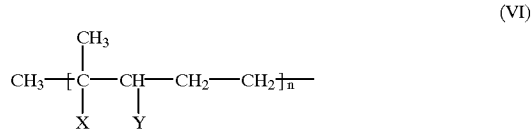
(VI)

in which n is an integer from 1 to 6 and either X and Y are both H, or X is methoxy and Y is H, or else X and Y together are an additional bond between the C atoms carrying X and Y, is used as unsaturated alcohol. The process is particularly important when the alcohol of the general formula II used is, for example, 3,7-dimethyl-1,6-octadien-3-ol (linalool), 3,7-dimethyl-1-octen-3-ol (dihydrolinalool), 3,7,11-trimethyl-1,6,10-dodecatrien-3-ol (nerolidol), 3,7,11-trimethyl-1-dodecen-3-ol or 3,7,11-trimethyl-1,6-dodecadien-3-ol (dihydronerolidol).

The reaction succeeds in principle with any alkyl acetoacetates, but the methyl ester, the ethyl ester and the isopropyl ester are preferred for both economic and technical reasons because the alcohols to be eliminated therefrom have particularly low boiling points and can thus be removed from the reaction mixture easily. However, mention should also be made of tert-butyl acetoacetate because with this the reaction takes place particularly quickly and free of byproducts.

Suitable organic aluminum compounds for the process according to the invention are compounds of the general formula V

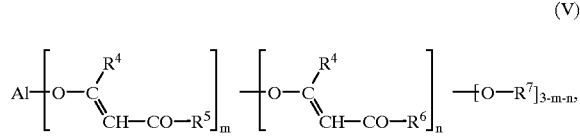
(V)

in which $R^4$ is alkyl or alkoxy groups having 1 to 4 C atoms, preferably methyl or ethyl groups, $R^5$ and $R^6$ are alkyl or alkoxy groups having 1 to 5 C atoms, preferably a methyl or a 2-butyl group, $R^7$ is an alkyl group having 1 to 4 C atoms, and m and n may each be an integer from 0 to 3, where $n+m \leq 3$, or else aluminum triaryloxide.

Very particular preference is given to liquid aluminum compounds in which $R^5$ is a methyl radical and $R^6$ is a butyl radical, the total $n+m=3$ and the ratio $n/m>0.3$.

Thus, the first-mentioned catalysts are lower aluminum trialcoholates such as aluminum trimethoxide, triethoxide, triisopropoxide and tri-sec-butoxide, and compounds formed on reaction of said aluminum trialcoholates with stoichiometric amounts of acetylacetonate, alkyl acetoacetate or alkyl malonate with elimination of alcohol and transesterification. Examples which may be mentioned are aluminum triacetoacetate, aluminum triacetylacetonate, aluminum monoacetoacetate diethoxide, aluminum monoacetoacetate diisopropoxide, aluminum diacetoacetate monoisopropoxide. The aluminum trialcoholates are preferably used, in particular aluminum triisopropoxide and aluminium tri-sec-butoxide. Very particular preference is given to the use of the mixed aluminum triacetoacetate obtained by reacting aluminium tri-sec-butoxide with methyl acetoacetate with elimination of 2-butanol and transesterification of the methoxy groups with the liberated 2-butanol, the degree of transesterification being more than 30%. We use the term aluminum triaryloxides for the aluminum salts of aromatic hydroxyl compounds such as aluminum triphenolate, aluminum tricresolates, aluminum trixylenolates, aluminum trinaphtholates, in which the aryl radicals can also be substituted by lower alkyl or alkoxy groups, i.e. alkyl or alkoxy groups having 1 to 4 C atoms, hydroxyl groups or phenyl. Aluminum triphenolate is relatively easily obtained and is particularly advantageously used.

The amount of aluminum compound is generally such that its concentration in the reaction mixture is not less than 0.05% by weight Al, and does not exceed 6% by weight Al at the start of the reaction. In general, 0.5 to 5 mol % of the aluminum compound are required, based on alkyl acetoacetate to be reacted. The amounts employed of the aluminum triisopropoxide which is preferably used and of the mixed aluminum triacetoacetate which is described above and prepared from aluminum tri-sec-butoxide and methyl acetoacetate are, for example, about 1 to 3 mol % based on the alkyl acetoacetate to be reacted.

Re A

The term solvent used in feature A of the claim means both conventional inert solvents as employed in Carroll reactions, and the liquids which are referred to in DE 2 928 944 as "intermediate boilers" and have a boiling point between that of the alkyl acetoacetate of the general formula III and that of the alcohol of the general formula IV to be eliminated therefrom.

The term "effective amounts of a solvent" means according to the invention less than about 10% by weight, preferably less than 3% by weight, for the conventional solvents, but less than 0.5% for the liquids which are employed in smaller quantities and are referred to as "intermediate boilers".

Re B

A reaction temperature which is as constant as possible at between 175 and 220° C., preferably 180 and 200° C., can be adjusted in the process according to the invention either by varying the heat input and/or where appropriate the pressure and/or by varying the rate of addition of the alkyl acetoacetate. The usual heat input is between 1 and 100 kW/m³ of reaction solution, preferably between 5 and 50 kW/m³. The pressure should be between 0.1 and 6 bar, preferably between 0.5 and 2 bar.

In addition or as alternative to varying the heat input and/or the pressure, it is also possible to utilize deliberate feeding in of an inert gas, which is heated where appropriate, for stripping out the alcohol and thus for influencing the reaction temperature as required. Particularly suitable for this purpose is partial or complete return of the carbon dioxide liberated in the Carroll reaction. The amount of inert gas metered in should for this purpose be between 1 and 100 m³(STP) of gas per h and m³ of reactor volume, preferably between 5 and 25 m³(STP)/(h*m³).

It is also possible and worthwhile to vary the metered amount of alkyl acetoacetate over time to achieve a constant temperature in the reaction solution.

It is also an advantage for carrying out the process according to the invention to ensure adequate mixing of the reaction mixture in the reaction vessel. This can be achieved, for example, with the aid of a stirrer, by pumping the reaction mixture through an external liquid circulation, by introducing the alkyl acetoacetate by means of a mixing nozzle and/or else by passing in a stream of inert gas.

It is also advisable, for improving the mixing of the reaction mixture and to facilitate the removal by distillation of the alcohol of the general formula IV formed in the reaction, to pass an inert gas into the reaction vessel and/or return the carbon dioxide formed in the reaction to the reaction vessel. It is additionally possible to use a mixing nozzle to intensify the mixing. If the reaction mixture is pumped through an external liquid circulation then it should be exchanged between 1 and 100 times per hour, preferably between 5 and 20 times per hour, through the external liquid circulation.

The acetoacetate should be metered directly into the liquid circulation for thorough mixing. If an additional heat input is desired, a heat exchanger can be provided in the liquid circulation, in addition to the heating of the reaction vessel.

The process according to the invention can be carried out both batchwise and continuously.

DESCRIPTION OF THE DRAWINGS

Carrying out the process according to the invention batchwise (cf.

Figure 1:
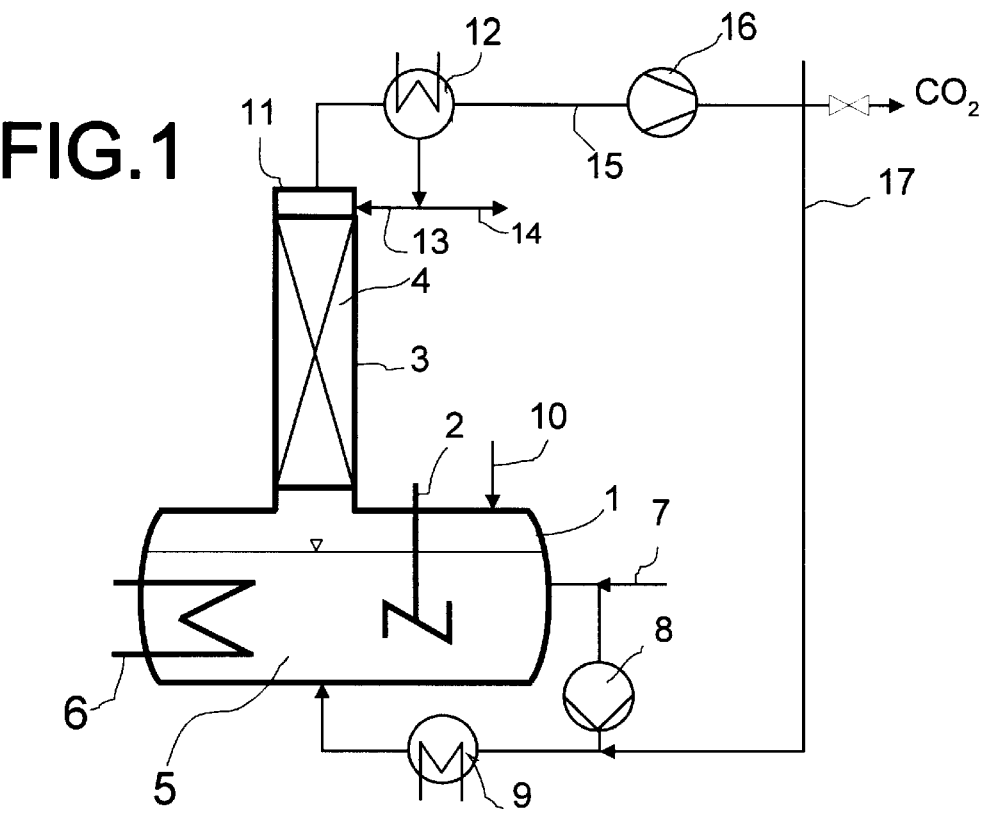
FIG. 1).

An example of a suitable reactor system for the batchwise reaction is the conventional heated reaction vessel (1) depicted in FIG. 1, with stirrer (2) and fitted fractionation column (3), in particular with a column with about 2 to 40 theoretical plates. Suitable for this purpose are all types of column internals (4) such as ordered packings, trays of various designs or random packings. The temperature in the reaction system can be maintained at the required level by varying the heat input, by changing the pressure, by feeding in heated or cooled inert gas and/or by a suitable variable metering of the alkyl acetoacetate.

According to the invention, the unsaturated alcohol of the formula II is introduced, where appropriate together with the organic aluminum compound used as catalyst, into the reaction vessel (1). It is advantageous additionally to introduce about 5% by weight of the alcohol of the general formula IV in order to avoid the risk of delayed boiling. The vessel contents (5) are heated for example with a heating element as heat source (6) or with a heat exchanger (9) installed in the external circulation (7) with pump (8). After adjustment to the required reaction temperature, the alkyl acetoacetate of the formula III is metered through a feed line (10) into the reaction vessel (1) or into the external circulation (7) in such a way that the content of alkyl acetoacetate is kept as constant as possible at between 0.5 and 10% by weight, preferably between 1 and 3% by weight, in the reaction solution (5).

As the metering of the alkyl acetoacetate is started, the formation of alcohol of the general formula $R^3$-OH and carbon dioxide begins. These reaction products are removed with the aid of the fitted column (3) at the top (11) of the column and passed into the condenser (12). Part of the alcohol $R^3$-OH which has condensed out is returned to the column (3) through return line (13), and the other part is taken off as distillate at the outlet (14). The carbon dioxide (15) leaving the condenser can, for the reasons stated above, be completely or partly returned with the aid of a compressor (16) via the gas line (17) to the reaction vessel (1). The metering of the alkyl acetoacetate through the feed line (10) generally takes about 2 to 4 hours (h). If quantitative conversion of the alkyl acetoacetate is desired, it is advantageous to keep the reaction mixture at the reaction temperature for about 1 to 2 h after the feeding in is complete. The progress of the reaction can be followed by the evolution of carbon dioxide (15) and/or by the amount of alcohol (14) eliminated from the alkyl acetoacetate. The concentration of the alkyl acetoacetate in the reaction mixture (5) can be determined by gas chromatographic analysis.

Figure 2:
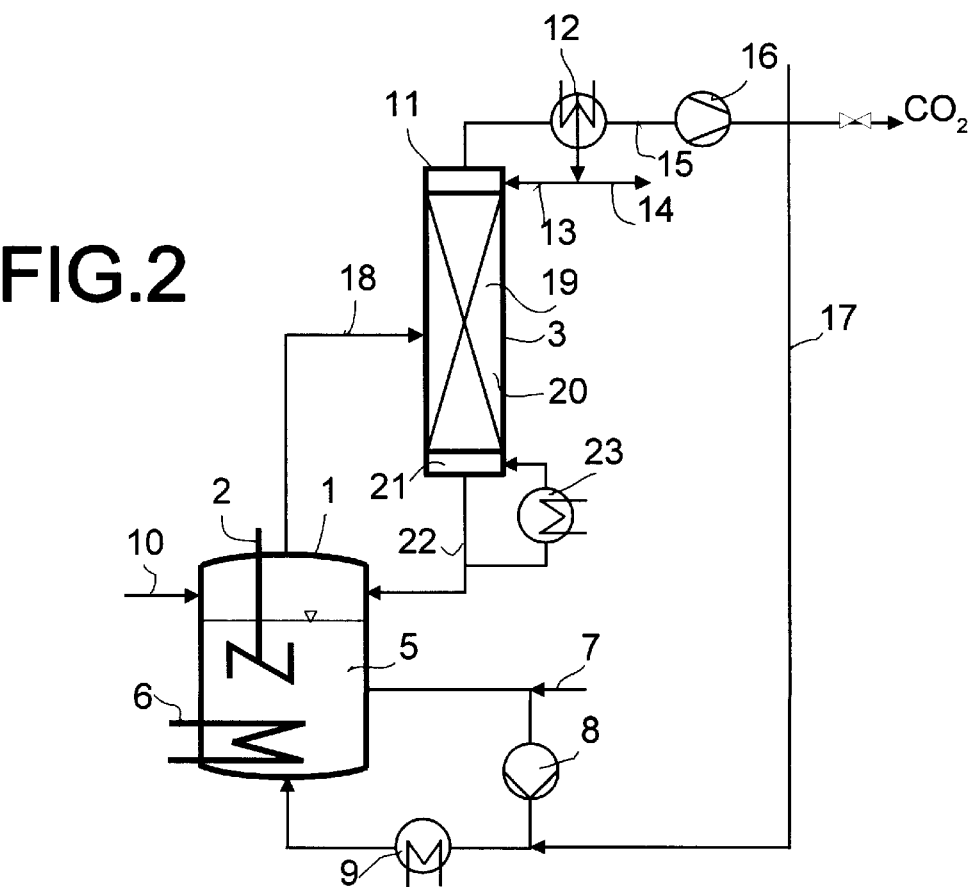

Alternative batchwise procedure as shown in FIG. 2:

A possible variant of the procedure described above is to carry out the reaction in a reaction vessel (1) with a not directly fitted fractionating column (3), as depicted in FIG. 2. Once again, the reaction vessel (1) is equipped where appropriate with a stirrer (2) and a heating element as heat source (6) and, where appropriate, with an external circulation (7) comprising a pump (8) and, where appropriate, a heat source (9). The alkyl acetoacetate is metered in through the feed line (10). The vapors (18) emerging from the reaction vessel (1) are passed into a column (3) with enriching section (19) and stripping section (20). In this case, the resulting carbon dioxide is removed together with the resulting alcohol at the top of the column (11) and passed into the condenser (12). In analogy to the variant described above, the alcohol $R^3$OH is condensed out and part of it is introduced into the column through return line (13), and the other part is removed at the outlet (14). It is likewise possible for the carbon dioxide (15) leaving the condenser (12) to be returned to the reaction vessel (1) through line (17) with a compressor (16), or be removed from the reaction circulation. The unreacted reactants leaving the bottom (21) of the column (3) through outflow line (22) are returned to the reaction vessel (1) and/or returned, after heating in a heat source (23), to the lower part of the column. The metering and reaction are carried out as in the process described above.

Figure 3:
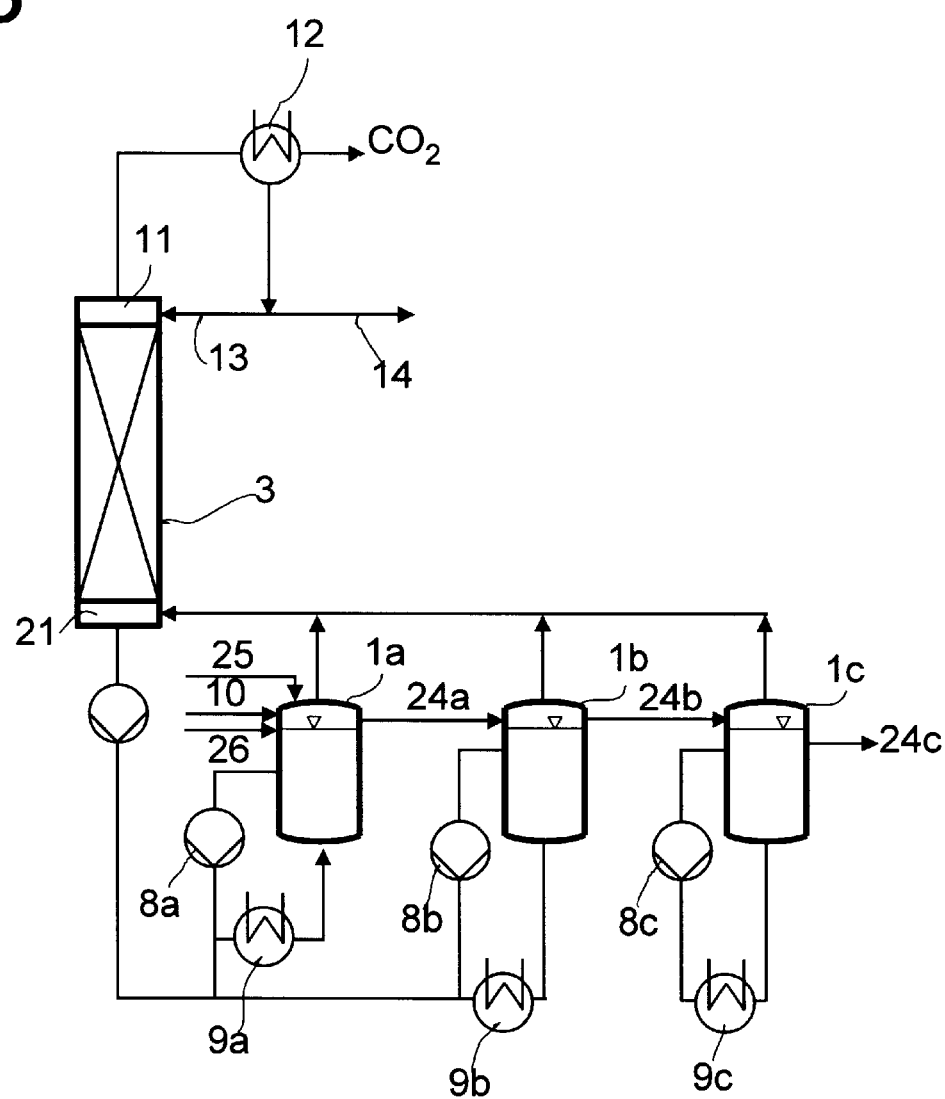

Continuous reaction (cf. FIG. 3):

In a continuous procedure it is possible to use as reactor system for example a heated vessel cascade with 1 to 10, expediently with 2 to 4, vessels. In this case, the individual vessels (e.g. 1a–1c) are connected together by the overflow lines (e.g. 24a–24c). A separate column can be fitted to each vessel or else—as depicted in FIG. 3—only one column (3) is fitted for all vessels. The reactants are continuously introduced into the first vessel (1a), specifically the alcohols of the general formula II through the feed line (25), the alkyl acetoacetate through the feed line (10) and, where appropriate, the aluminum catalyst through the feed line (26). The maintenance of the required reaction temperature and the manner of operating the column (3) are essentially the same as for the batchwise procedure.

It is possible with the aid of the process improved according to the invention to prepare numerous higher ketones, in particular those ketones required for preparing isophytol and thus for preparing vitamin E, such as geranylacetone, farnesylacetone, 6,10-dimethyl-5-undecen-2-one and 6,10,14-trimethyl-5,9-pentadecadien-2-one, with virtually quantitative conversion in very high yields and space-time yields, and high purity.

EXAMPLE 1

A Preparation of 6,10-dimethyl-5-undecen-2-one (dihydrogeranylacetone: H-GAC) starting from 3,7-dimethyl-1-octen-3-ol (H-LIN) without inert gas feeding in The experimental apparatus consisted of an electrically heatable 4 liter round-bottomed flask made of glass and equipped with a stirrer and fitted with a distillation column with an internal diameter of 30 mm. The round-bottomed flask was provided with appropriate ports for metering the reactants and for sampling. The column had a 1 meter-high packing of 5 mm stainless steel wire helices. The reactants were either present in the reaction vessels from the outset or metered in by a pump under mass flow control from a receiver. The methanol and $CO_2$ liberated during the reaction were removed through the column and condensed in a partial condenser. The condensate ran through a reflux divider into a receiver. The remaining exit gas stream was passed through a cold trap and then removed through a gas meter to measure the volume. The laboratory apparatus was completely automated so that all material inflows and outflows could be continuously measured and recorded throughout the experiment.

31.0 g of aluminum triisopropoxide (1.54 mol % based on the total amount of methyl acetoacetate) were mixed in a 500 ml stirred flask with 77.3 g of H-LIN (94% pure; 0.47 mol calculated to 100%) and 17.6 g (0.15 mol) of methyl acetoacetate (MAA) and heated to 150° C.

Then 1513.7 g of H-LIN (94% pure; 9.12 mol calculated to 100%) were introduced into the reaction flask with fitted column and heated to 100° C. The catalyst solution at 150° C. was then mixed with the H-LIN at 100° C. in the reaction vessel, and the resulting mixture was then heated to 175° C. Over the course of 3.5 hours (h), 1116.4 g (9.62 mol) of MAA were metered into this. During the MAA addition, the reaction solution was heated further and the temperature was controlled at 185° C. When the MAA addition was started, the evolution of $CO_2$ began and the methanol which was formed was taken off as distillate at the top of the column. When the MAA metering ceased, the after-reaction started. The temperature was also kept constant at 185° C. during the after-reaction, which was complete after 1 h. The 6,10-dimethyl-5-undecen-2-one (H-GAC) was obtained in a yield of 93.0% of theory based on h-LIN and 91.1% of theory based on MAA. The selectivity was 97.4% of theory based on reacted H-LIN and 91.1% of theory based on MAA (the conversion was 100% based on MAA).

EXAMPLE 2

Preparation of 6,10-dimethyl-5-undecen-2-one (H-GAC) starting from H-LIN with inert gas feeding in Experiments 2b and 2d indicated in Table 1 were carried out in the manner described in Example 1A but with additional feeding in of inert gas. In this case, when the MAA metering started, $CO_2$ was metered from a gas cylinder into the reaction vessel and maintained until the after-reaction phase was complete. The inert gas feeding in on the one hand promoted mixing of the reaction mixture and thus avoided the risk of delayed boiling, and on the other hand the resulting methanol was stripped out.

The experimental results obtained in these examples 2b and 2d are shown in Table 1 below, comparing with corresponding experiments without inert gas feeding in (Examples 2a and 2c). The results clearly show that the reaction time necessary for complete MAA conversion is reduced by the inert gas feeding in.

TABLE 1

Comparison of experiments with and without inert gas feeding in

| Example | Catalyst [mol %] | H-LIN/MAA feed [mol/mol] | Yield of H-GAC [%] | After-reaction time [h] | Inert gas feeding in |
|---|---|---|---|---|---|
| 2a | 1.80 | 1.0 | 92.9 | 1.0 | none |
| 2b | 1.80 | 1.0 | 92.6 | 0.0 | with $CO_2$ |
| 2c | 1.35 | 1.0 | 89.8 | 1.0 | none |
| 2d | 1.35 | 1.0 | 90.0 | 0.0 | with $CO_2$ |

EXAMPLE 3

Preparation of 6,10,14-trimethyl-5,9-pentadecadien-2-one (dihydrofarnesylacetone)

The experimental apparatus consisted of a heatable stainless steel 2 liter reaction flask equipped with stirrer and fitted with a distillation column (length: 1 m, diameter: 25 mm). The column was packed with stainless steel wire helices (5 mm). The reactants were either present in the reaction vessels from the outset or metered in by a pump. The methanol and $CO_2$ liberated during the reaction were removed through the column and condensed. All material inflows and outflows were measured and recorded continuously throughout the experiment to permit a time-dependent mass balance.

7.5 g of aluminum triisopropoxide (1.25 mol % based on total amount of MAA) were mixed in a 100 ml round-bottomed flask with 35.4 g of 3,7,11-trimethyl-3-hydroxy-1,6-dodecadiene (93% pure, 0.15 mol calculated to 100%) and 7.5 g (0.06 mol) of MAA, and the mixture was heated to 150° C. Then 657.6 g of 3,7,11-trimethyl-3-hydroxy-1,6-dodecadiene (93% pure, 2.73 mol calculated to 100%) were introduced into the reaction flask with fitted column and heated to 100° C. The catalyst solution at 150° C. was then mixed with the 3,7,11-trimethyl-3-hydroxy-1,6-dodecadiene at 100° C. in the reaction vessel and heated to 175° C. Then 326.5 g (2.81 mol) of MAA were metered over the course of 3.5 h into the reaction vessel. During the MAA addition, the reaction solution was heated further and the temperature was controlled at 185° C. When the MAA addition was started, the evolution of $CO_2$ began. The methanol which was formed was taken off as distillate at the top of the column. The reflux ratio was 0.1; When the MAA metering ceased, the after-reaction started. The temperature was also kept constant at 185° C. during the 2-hour after-reaction. The 6,10,14-trimethyl-5,10-pentadecadien-2-one was obtained in a yield of 89.3% based on 3,7,11-trimethyl-3-hydroxy-1,6-dodecadiene and 89.3% based on MAA. The selectivity was 93.8% based on 3,7,11-trimethyl-3-hydroxy-1,6-dodecadiene and 89.8% based on MAA (the conversion was 100% based on MAA).

We claim:
1. A process for preparing unsaturated ketones of formula I:

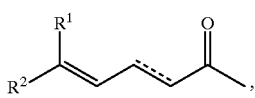

(I)

in which the dotted line is an optional additional C—C bond, $R^1$ is an alkyl group having 1 to 4 C atoms, and $R^2$ is a saturated or unsaturated aliphatic, cycloaliphatic or cycloaliphatic-aliphatic radical having 4 to 30 C atoms, by reacting the corresponding α,β-unsaturated alcohols of formula II:

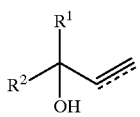

(II)

with alkyl acetoacetates of formula III:

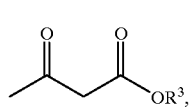

(III)

in which $R^3$ is an alkyl having 1 to 4 carbon atoms, in the presence of from 0.1 to 5 mol. %, based on the alkyl acetoacetate to be reacted, of an organic aluminum compound as catalyst with elimination and continuous removal by distillation of the carbon dioxide which forms during the reaction and of the alcohol of formula IV:

$R^3$—OH   (IV)

which is eliminated from the acetoacetate in a reactor system with a fitted fractionation column, wherein
  A an α,β-unsaturated alcohol is introduced into the reaction vessel together with the organic aluminum compound in the absence of effective amounts of a solvent or anintermediate boiler, and the alkyl acetoacetate is metered into this mixture,
  B a reaction temperature which is as constant as possible at between 175° C. and 220° C. is adjusted, and
  C during the reaction the content of alkyl acetoacetate in the reaction mixture is adjusted to a value which is as constant as possible at between 0.1 and 10% by weight.

2. A process as claimed in claim 1, wherein a reaction temperature which is as constant as possible at between 180° C. and 200° C. is adjusted in B.

3. A process as claimed in claim 1, wherein an aluminum compound of the general formula V

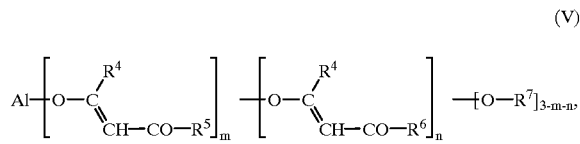

(V)

in which $R^4$ is an alkyl or alkoxy group having 1 to 4 C atoms, $R^5$ and $R^6$ are alkyl or alkoxy groups having 1 to 5

C atoms, $R^7$ is an alkyl group having 1 to 4 C atoms, and m and n may each be an integer from 0 to 3, where n+m≦3, or else an aluminum triaryloxide is used as organic aluminum compound.

4. A process as claimed in claim 1, wherein the amounts of the reactants employed are chosen to result in a molar ratio of alcohol to alkyl acetoacetate of between 0.7 and 1.2.

5. A process as claimed in claim 1, wherein the amounts of the reactants employed are chosen to result in a molar ratio of alcohol to alkyl acetoacetate of between 0.95 and 1.05.

6. A process as claimed in claim 1, wherein an inert gas is passed into the reaction vessel and/or the carbon dioxide formed in the reaction is returned to the reaction vessel in order to improve the mixing of the reaction mixture and to facilitate the removal by distillation of the alcohol of the general formula IV formed in the reaction.

7. A process as claimed in claim 1, wherein the reaction temperature defined in B is controlled by suitable variation of the heat input and/or by variation of the rate of addition of the alkyl acetoacetate.

8. A process as claimed in claim 1, wherein adequate mixing of the reaction mixture in the reaction vessel is ensured by use of a stirrer, by pumping the reaction mixture through an external liquid circulation, by introducing the alkyl acetoacetate by means of a mixing nozzle or else by passing in a stream of inert gas.

9. A process as claimed in claim 1, wherein an alcohol of the general formula II in which $R^1$ is an alkyl group having 1 to 4 C atoms and $R^2$ is a group of the general formula VI

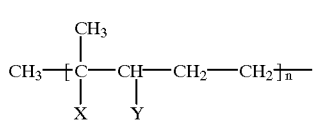

(VI)

in which n is an integer from 1 to 6 and either X and Y are both H, or X is methoxy and Y is H, or else X and Y together are an additional bond between the C atoms carrying X and Y, is used as unsaturated alcohol.

10. A process as claimed in claim 9, wherein 3,7-dimethyl-1,6-octadien-3-ol (linalool), 3,7-dimethyl-1-octen-3-ol (dihydrolinalool), 3,7,11-trimethyl-1,6,10-dodecatrien-3-ol (nerolidol), 3,7,11-trimethyl-1-dodecen-3-ol or 3,7,11-trimethyl-1,6-dodecadien-3-ol (dihydronerolidol) is used as alcohol of the general formula II.

* * * * *